(12) United States Patent
Ritchie

(10) Patent No.: US 8,307,463 B2
(45) Date of Patent: Nov. 13, 2012

(54) HANDS-FREE PUMPING AND NURSING BRA OR TANK

(76) Inventor: Jennifer Ritchie, Laguna Niguel, CA (US)

(*) Notice: Subject to any disclaimer, the term of this patent is extended or adjusted under 35 U.S.C. 154(b) by 324 days.

(21) Appl. No.: 12/821,188

(22) Filed: Jun. 23, 2010

(65) Prior Publication Data

US 2011/0314587 A1    Dec. 29, 2011

(51) Int. Cl.
*A41D 1/20*    (2006.01)

(52) U.S. Cl. ............ 2/104; 450/36; 604/73

(58) Field of Classification Search ............ 2/73, 78.1, 2/104–106, 108–110, 113–115, 119–121; 450/36, 37; 604/73–76, 385.07, 383

See application file for complete search history.

(56) References Cited

U.S. PATENT DOCUMENTS

| | | | |
|---|---|---|---|
| 5,575,768 A * | 11/1996 | Lockridge et al. | 604/74 |
| 6,004,186 A | 12/1999 | Penny | |
| 6,213,840 B1 | 4/2001 | Han | |
| 6,227,936 B1 | 5/2001 | Mendoza | |
| 6,247,996 B1 * | 6/2001 | Fields | 450/36 |
| 6,855,029 B2 * | 2/2005 | Rothman | 450/36 |
| 6,887,217 B1 | 5/2005 | Logan | |
| 7,076,809 B2 | 7/2006 | Rothman | |
| 7,094,217 B2 | 8/2006 | Fialkoff | |
| 7,607,965 B1 | 10/2009 | Frazier | |
| 8,075,369 B2 * | 12/2011 | Hendrickson | 450/86 |
| 2007/0074330 A1 * | 4/2007 | Azaronak | 2/104 |
| 2008/0022434 A1 * | 1/2008 | Adelman | 2/104 |
| 2008/0064299 A1 * | 3/2008 | La Fontaine | 450/36 |

* cited by examiner

*Primary Examiner* — Katherine Moran

(57) ABSTRACT

This invention relates generally to a bra or tank that has three layers on the chest that allow the wearer to comfortably breast feed or pump milk hands-free. Specifically, the tank or bra has three detachable layers over the breast where the outer layer is a solid layer, the inner layer has two openings over the nipple that are equipped to receive the funnels of a breast pumping apparatus and hold them to the breast without the wearer holding them, and an inner layer that has a large opening for the breast so that the wearer may breast feed an infant.

19 Claims, 5 Drawing Sheets

HANDS-FREE PUMPING AND NURSING BRA OR TANK

FIELD OF THE INVENTION

This invention relates generally to a bra or tank that has three layers on the chest that allow the wearer to comfortably breast feed or pump milk hands-free. Specifically, the tank or bra has three detachable layers over the breast where the outer layer is a solid layer, the inner layer has two openings over the nipple that are equipped to receive the funnels of a breast pumping apparatus and hold them to the breast without the wearer holding them, and an inner layer that has a large opening for the breast so that the wearer may breast feed an infant.

BACKGROUND

Breast milk offers several advantages over manufactured formula as a food source for infants. It is well known that the American Academy of Pediatrics recommends that women breastfeed their infants for at least one year. During this time, it is advantageous for the breastfeeding woman to have garments that facilitate breastfeeding, and breast pumping when a woman cannot nurse her infant. While many women are able to nurse their infants directly from their breast, there are many reasons a woman may need or choose to pump milk for her child.

Many women re-enter the workforce soon after childbirth and want to continue breastfeeding. Other women would like to pump their milk to give to the infant when they are uncomfortable or unable to directly nurse their babies. For many reasons, many mothers use a breast pump. As is well known, breast pumps (manual and electric) use a conical pump funnel that is in direct contact with the breast to pump milk from the breast. The funnels must be held in place over the breast during the pumping process, otherwise they fall off when suction is lost.

Several brassieres and other garments have been developed that hold the funnel to the breast so that the mother does not need to hold the funnels while pumping (see U.S. Pat. Nos. 7,094,217, and 6,227,936). Many of these garments do not effectively hold the pump funnels in place, are uncomfortable, or are impractical for daily wear. There is currently no garment that allows the wearer both to pump hands-free, and nurse her infant through the use of several detachable layers that cover the breast area. Additionally, no garment that allows for hands-free pumping and nursing is comfortable and practical for daily wear currently exists.

Thus, there is a need for a garment that is either a bra or a tank that a woman can wear throughout the day that allows for hands-free pumping and allows the woman to breast feed, while providing comfort and discretion.

SUMMARY OF THE INVENTION

According to one aspect of the present invention, the hands-free pumping and nursing bra or tank is a comfortable and practical garment that allows a woman to pump her milk and/or nurse an infant while wearing the garment.

According to another aspect of the present invention, the hands-free pumping and nursing bra or tank provides support for the breasts of the wearer with an elastic portion that is positioned under the breast and extends around the circumference of the body, the elastic portion also connecting the middle and inner layer of the bra/tank.

Additionally, according to yet another aspect of the present invention, the hands-free pumping and nursing bra or tank provides an outer layer over the bust that is thicker than a single layer of fabric for comfort and discretion. The outer layer is connected to the straps of the tank by a clasp or other attachment means.

Moreover, in another aspect of the present invention, the pumping and nursing tank or bra has a middle layer of fabric that has an opening over each nipple that is capable of receiving the funnel portion of a pumping device so that the wearer can pump hands-free. The middle layer is detachable from the inner layer by clasps or other attachment means, and is connected to the inner layer at the center of the chest with stitching.

In yet another aspect of the present invention, the hands-free pumping and nursing tank or bra has an inner layer that has a larger opening over each breast so that the outer and middle layer may be detached, and the woman can nurse and infant through the opening.

An object of the present invention is to provide a garment that can be worn as a top and brassiere at the same time.

Another object of the present invention is to provide a garment that provides support to the breasts of the wearer and allows the wearer to nurse and pump in comfort.

Yet another object of the present invention is to provide a convenient and comfortable garment for breastfeeding mothers to wear on a daily basis.

BRIEF DESCRIPTION OF THE DRAWINGS

The foregoing aspects and many of the accompanying advantages of this invention will become more readily appreciated as the same becomes understood by reference to the following detailed description, when taken in conjunction with the accompanying drawings, wherein.

DETAILED DESCRIPTION

The invention described in detail herein generally relates to nursing apparel for women.

The garment of the present invention can be either a brassiere or tank top that can be worn while pumping without hand support, or nursing and infant. When not pumping or nursing, an outer layer is aesthetically pleasing and can be worn as a top or under garment (See FIGS. 2 and 3). The use of the term bra is synonymous with tank or other tops that can incorporate the three layers discussed while supporting the breast.

Figure 1:
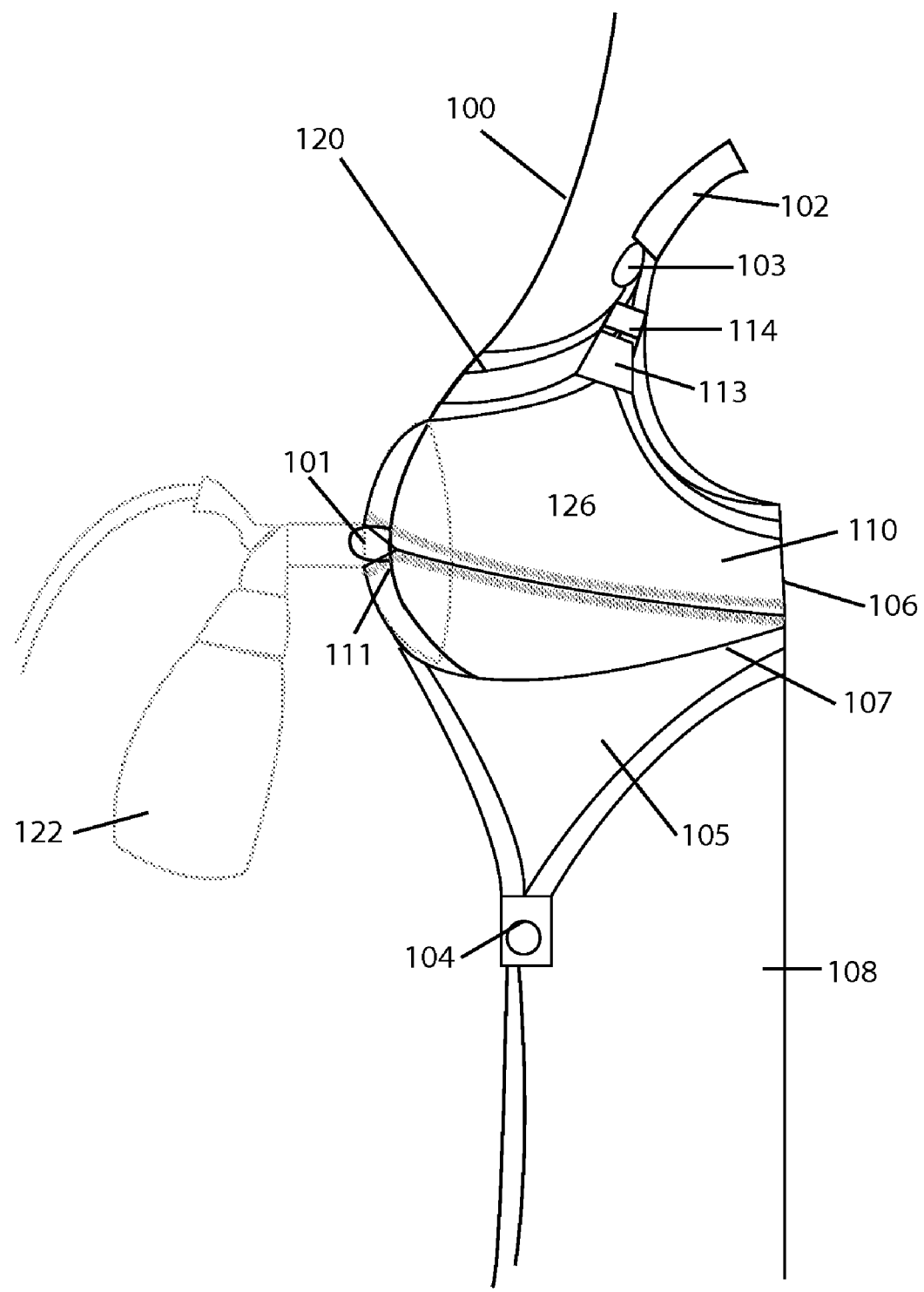
FIG. 1 is a side view of the nursing tank with a pumping device attached to the breast, as in one embodiment of the present invention.
Figure 2:
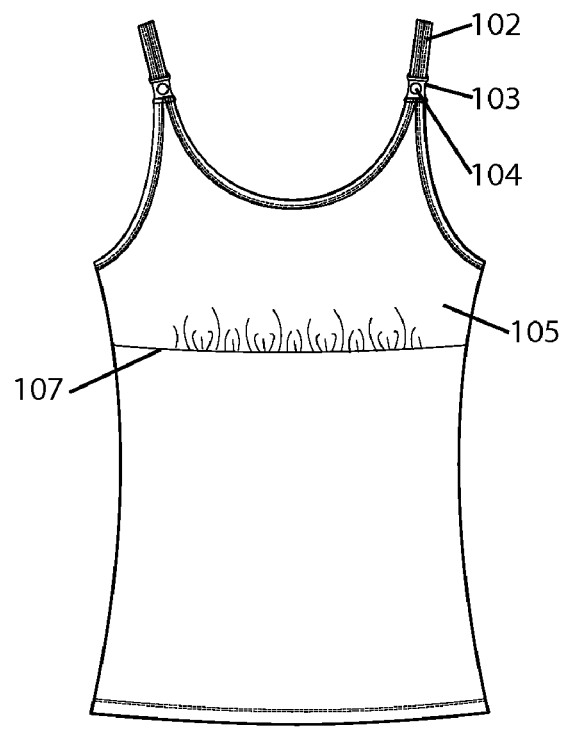
FIG. 2 is a front view of the nursing tank, according to one embodiment of the present invention.
Figure 3:
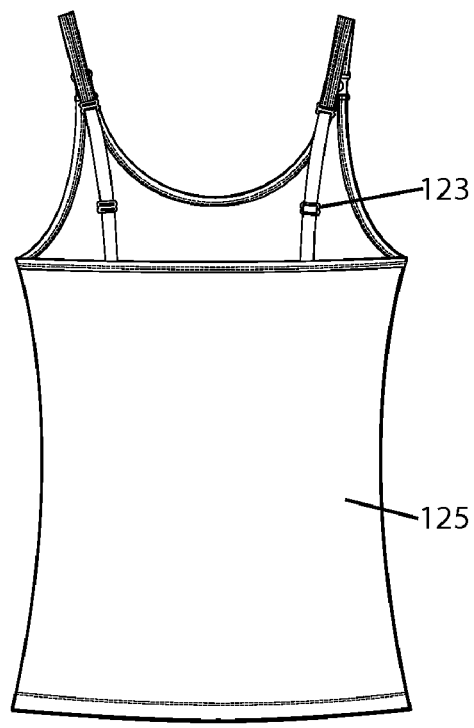
FIG. 3 is a back view of the nursing tank, as in one embodiment of the present invention.
Figure 9:
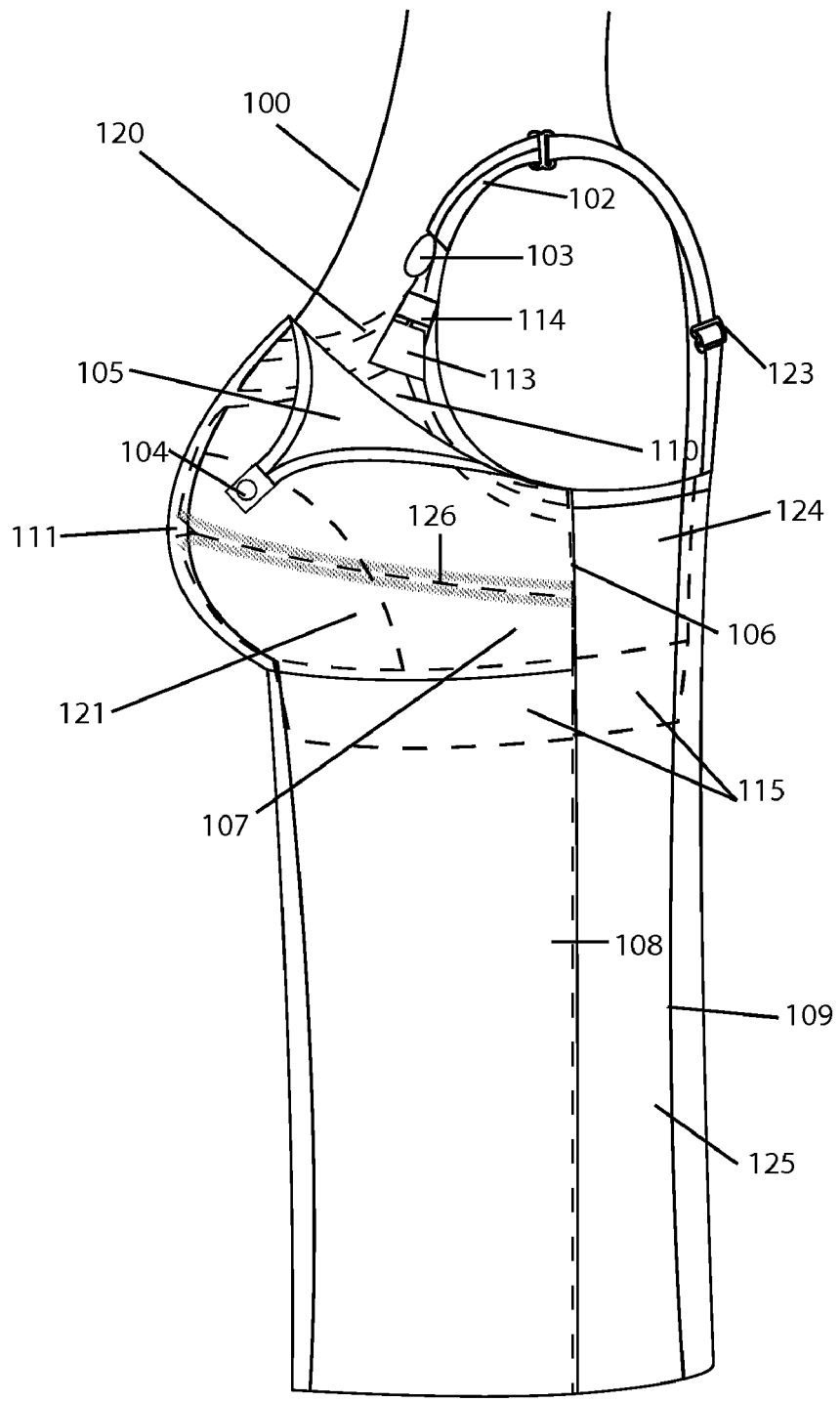
FIG. 9 is a side view of the nursing tank illustrating the three layers and elastic band that support the breasts, as in one embodiment of the present invention.

FIG. 1 illustrates the bra/top on a woman who is using a breast pump. The tank sits on the chest 100 and has two shoulder straps 102 that are adjustable in length 123 for the comfort of the wearer as is shown in FIGS. 2, 3 and 9. The shoulder straps 102 are connected to the inner layer 120 of the bra. Three layers, the inner layer 120, middle layer 110, and outer layer 105 comprise the bra of the present invention and allow the wearer to comfortably pump milk and/or nurse and infant while wearing the same garment.

Figure 4:
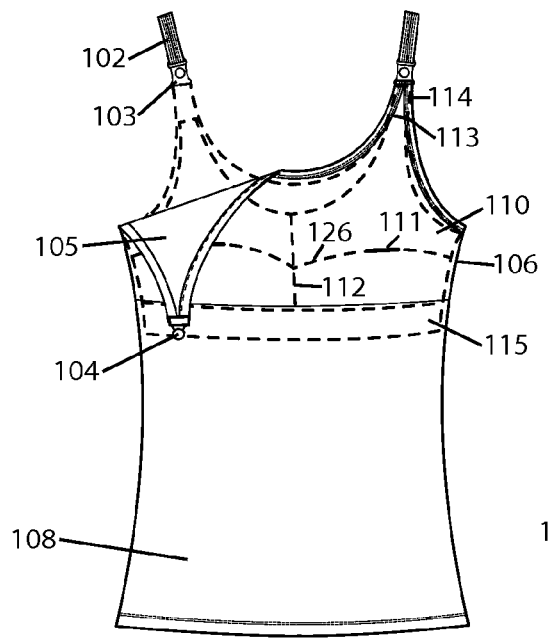
FIG. 4 is a front view of the nursing tank showing the outer and inner layer, according to one embodiment of the present invention.

The outer layer 105 is connected to each of the straps 102 with a clasp 103 and 104 or other fastening means that is easily detachable by the wearer. In the preferred embodiment, the clasp 103 and 104 is a circular male piece 103 that is attached to a sewn loop at the end of the strap 102. The circular male piece 103 fits into an oppositely shaped female piece 104 that is attached to a sewn loop in the outer layer 102. Other fastening means that are easily detachable may be used and do not depart from the scope of the invention. Each fastening means 103 and 104 can be open and closed independently, so that either one breast or both may be exposed at a time as shown in FIG. 4. When both fastening means 103 and 104 are detached, the outer layer can be completely folded down so that the chest of the wearer is exposed.

In one preferred embodiment the outer layer 105 is a double-layered fabric to enhance the opaqueness of the garment. The outer layer 105 is sewn to the bottom of the bust 107 where the garment is a top. In one preferred embodiment, the bottom of the outer layer 102 is sewn to the bottom of the bust 107 with a ruching effect that is aesthetically pleasing to the wearer as is illustrated in FIG. 2. Where the garment is a tank, the bottom of the bust 107 is connected to the bottom of the tank 108 that covers the abdominal region of the wearer as illustrated in FIGS. 1, 2, 3, and 9. Furthermore, when the garment is a top, a piece of fabric 125 is sewn at the sides to cover the back of the wearer (see FIG. 9).

Figure 5:
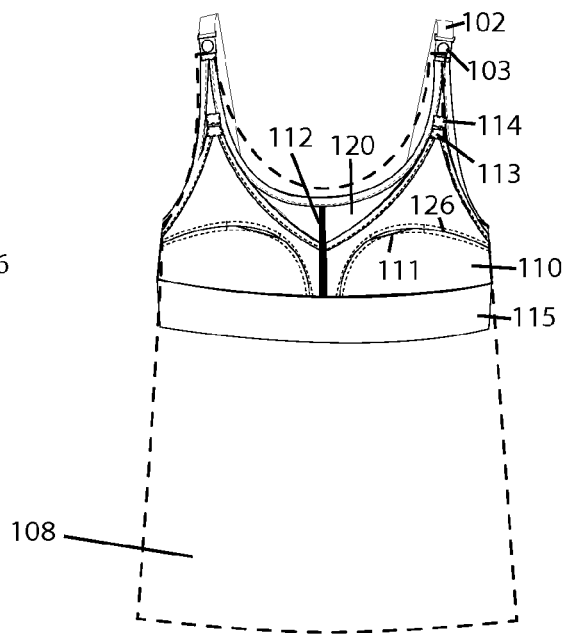
FIG. 5 is a front view of the middle layer of the nursing tank, as in one embodiment of the present invention.
Figure 7:
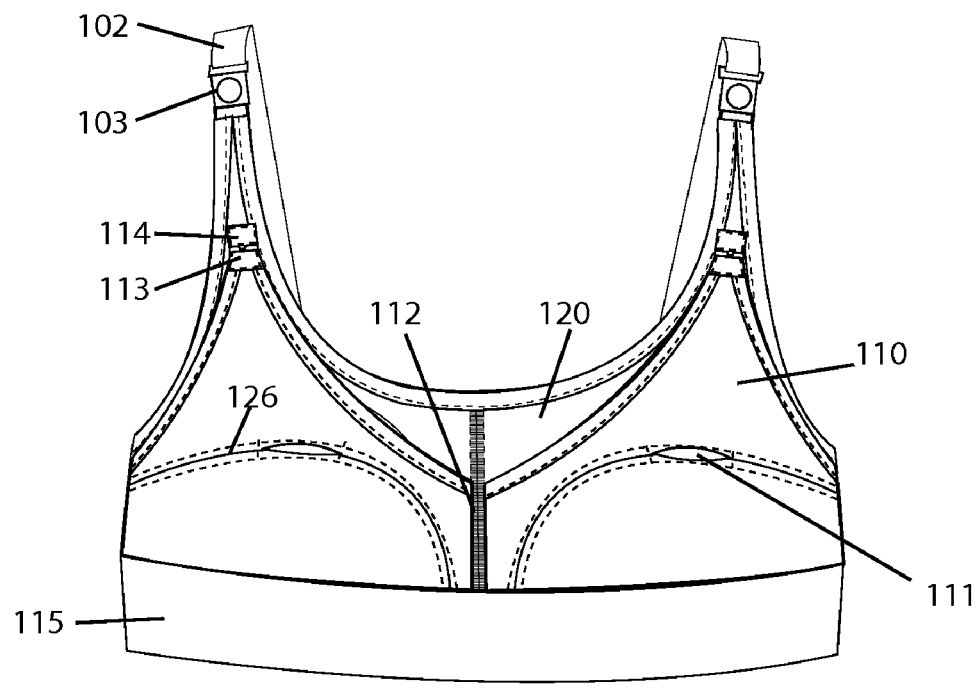
FIG. 7 is a front view of the nursing tank without the outer layer, detailing the middle layer and its relationship to the inner layer, as in one embodiment of the invention.

When the outer layer 102 is detached, the middle layer 110 is exposed. As shown in FIGS. 5 and 7, the middle layer 110 covers the breasts, with a small opening 111 over the nipple 101 of the wearer. In the preferred embodiment, the openings 111 are horizontal slits in the seaming of the bra 126 that are approximately one inch in length. The openings 111 are capable of receiving the funnel shaped portion of the breast pump 122, and holding it to the breast of the wearer during the pumping process (see FIG. 1). The horizontal slits 111 of the preferred embodiment are advantageous, as their shape and size are minimal enough to secure the funnels of the pump to the breast such that the wearer can pump without the assistance of her hands to hold them in place. Other shapes and sizes of openings 111 are contemplated and do not depart from the scope of the invention as long as they facilitate hands-free pumping for the wearer.

The middle layer 110 is connected to the inner layer 120 with a hook and eye clasp 114 and 113 in the preferred embodiment of the invention. The eye part of the clasp 114 is sewn onto the inner layer in the preferred embodiment of the invention. The hook 113 is sewn to the middle layer in the preferred embodiment of the invention. As in the preferred embodiment, two eyes 114 may be sewn to the inner layer 120 on each side for a customizable fit to the wearer. Other detachable clasps may be used to connect the middle layer 110 to the inner layer 120 without departing from the scope of the invention. As shown in FIG. 5 the middle layer 110 has seaming that extends from the lower portion of the breast, over the nipple, and under the armpit. The seaming forms an upside-down "U" shape in the preferred embodiment. The seaming imparts structural strength to the middle layer 110 that helps support the pumping apparatus.

The middle layer 110 is sewn to the inner layer 120 at the middle section 112 in the preferred embodiment as is shown in FIG. 5. This seaming 112 also adds to the structural integrity of the garment so that it can hold a pumping apparatus 122 to the wearer's breast without assistance.

The bottom of the middle layer 110 terminates in an elastic band 115 that extends around the chest of the wearer as shown in FIGS. 5, 7 and 9. The elastic band 115 in the preferred embodiment is 1.5 inches and holds the middle layer 110 and inner layer 120 under the breast. The elastic band 115 connects the bottom of both the middle layer 110, and inner layer 120. The middle layer 110 is sewn to the inner layer 120 at the sides of the wearer 106. The inner layer 120 can extend all the way around the wearer, with the elastic band 115 at the bottom, or another piece of fabric 124 that connects to the sides of the middle 110 and inner 120 layer and extends across the back of the wearer 109 with the elastic band 115 (see FIG. 9). The elastic band 115 supports the breasts of the wearer, as is the main function of a brassiere. Where the present invention is a top, a second piece of fabric 125 is outside of the inner layer 120 and back piece of fabric 124 that is connected to the elastic band 115.

Figure 6:
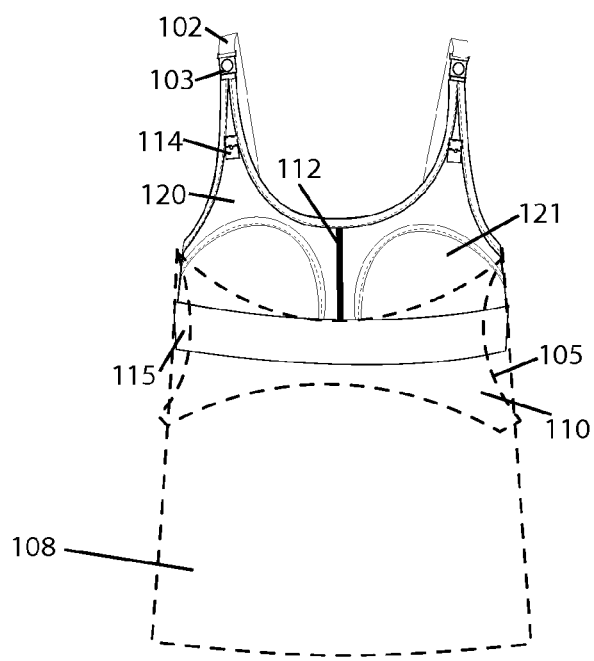
FIG. 6 is a front view of the inner layer of the nursing tank, according to one embodiment of the present invention.
Figure 8:
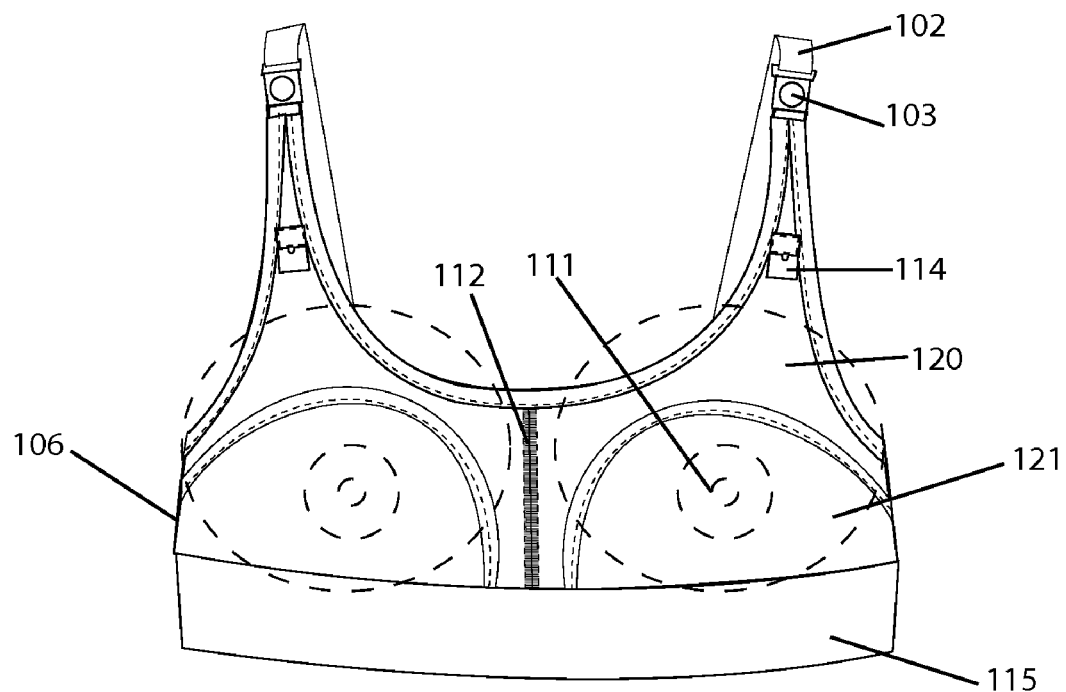
FIG. 8 is a front view of the nursing bra without the outer and middle layer, detailing the inner layer and the positioning of the breast within the bra, according to one embodiment of the present invention.

The inner layer 120 of the tank allows the wearer to nurse and infant through the large openings 121 over each breast as shown in FIGS. 6 and 8. The inner layer 120 is connected to the middle layer at the sides 106 of the garment, at the bottom where both layers are sewn to the elastic band 115, and in the middle of the chest with seaming 112, as in one preferred embodiment of the invention. When the outer layer 105 and middle layer 110 are detached, the wearer can expose the breasts to breastfeed. The wearer may choose to expose either one or both breasts.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein by reference, in their entirety, for background and to assist the reader of this disclosure.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

I claim:

1. A nursing garment comprising:
    at least two straps, one of said at least two straps being placed over one shoulder of a wearer and at least another of said at least two straps being placed over the other shoulder of the wearer, the said at least straps being adjustable in length, wherein a detachable clasp holds an outer layer to the straps and is coupled to each strap of said at least two straps, wherein each of said at least two straps terminate in an inner layer that is positioned over the breasts of the wearer, and the other end of said at least two straps terminates in fabric that covers the back of said wearer;

wherein said outer layer is a solid piece of fabric that covers the breasts of the wearer, said outer layer being sewn to the back of the garment at each side of the wearer, and at least two detachable clasps connect the outer layer to each of said at least two straps over each shoulder of the wearer;

a middle layer that is detachable by a clasp from the inner layer in at least two positions, each of said at least two positions being over each breast, the middle layer having at least one opening over each nipple of the wearer, said at least one opening being capable to receive a funnel portion of a breast pump and said one opening being able to support the funnel of the breast pump without assistance from the wearer when the middle layer is attached to the inner layer;

an inner layer having two large openings through which each nipple and breast may be exposed when the middle layer and outer layer are detached at said at least one of said detachable clasps of the outer layer and at least one of said at least two positions of the middle layer such that the wearer may nurse an infant;

wherein the inner and middle layer terminate in an elastic band that extends around the wearer to support the breasts.

2. The nursing garment of claim 1, wherein the garment is a brassiere.

3. The nursing garment of claim 1, wherein the garment is a tank.

4. The nursing garment of claim 1, wherein the detachable clasp comprises a male and female piece.

5. The nursing garment of claim 1, wherein the clasp at the at least two positions of the middle layer comprises a hook and eye closure.

6. The nursing garment of claim 3, wherein the outer layer terminates in a seam to an abdominal portion of the tank, wherein the outer layer and the abdominal portion of the tank are connected to a back piece of fabric of the tank, the back piece of fabric attached to the fabric that covers the back of said wearer.

7. The nursing garment of claim 1, wherein the at least one opening over each nipple of the wearer is approximately one inch in length.

8. The nursing garment of claim 1, wherein the at least one opening over each nipple of the wearer are horizontal.

9. The nursing garment of claim 1, wherein the elastic band is approximately one and one half inches in width.

10. The nursing garment of claim 1, wherein the inner layer and middle layer are connected with a seam that extends from the top of the inner layer to the elastic band in the middle of the wearer's chest.

11. A nursing garment comprising:

a first strap and a second strap, wherein each of the first and second straps being placed over each shoulder of a wearer and wherein a first and second detachable clasp couples an outer layer to the first and second straps, wherein the first detachable clasp couples the outer layer to the first strap, and the second detachable clasp couples the outer layer to the second strap and each of said first strap and said second strap are adjustable in length, and wherein each of the first and second straps terminate in an inner layer that is positioned over the breasts of the wearer, and the other end of the first and second straps terminates in a fabric that covers the back of said wearer;

wherein said outer layer is a solid piece of fabric that covers the breasts of the wearer, said outer layer being coupled to the fabric that covers the back of said wearer at each side of the wearer, and the detachable clasps connecting the outer layer to each of said the first and second straps over each shoulder of the wearer;

a middle layer that is detachable by a clasp from the inner layer in two positions, each of the two positions being over each breast, the middle layer having one horizontal opening over each nipple of the wearer that is approximately one inch in length, said one opening being capable to receive a funnel portion of a breast pump and said one opening being able to support the funnel of the breast pump without assistance from the wearer when the middle layer is attached to the inner layer;

an inner layer having a two large openings through which each nipple and breast may be exposed when the middle layer and outer layer are detached at the detachable clasps such that the wearer may nurse an infant;

wherein the inner and middle layer terminate in an elastic band that extends around the wearer to support the breasts, and the middle layer is attached to the inner layer with a seam located in the middle of the chest of the wearer, the seam extending from the top of the inner layer to the elastic band.

12. The nursing garment of claim 11, wherein the garment is a brassiere.

13. The nursing garment of claim 11, wherein the garment is a tank.

14. The nursing garment of claim 11, wherein the detachable clasp comprises a male and female piece.

15. The nursing garment of claim 11, wherein the clasp at the at least two positions of the middle layer comprises a hook and eye closure.

16. The nursing garment of claim 13, wherein the outer layer terminates in a seam to an abdominal portion of the tank, wherein the outer layer and the abdominal portion of the tank are connected to a back piece of fabric of the tank.

17. A nursing tank comprising:

a first strap and a second strap, wherein each of the first and second straps being placed over each shoulder of a wearer and wherein a first and second detachable clasp couples an outer layer to the first and second straps, wherein the first detachable clasp couples the outer layer to the first strap, and the second detachable clasp couples the outer layer to the second strap and each of said first strap and said second strap are adjustable in length, and wherein each of the first and second straps terminate in an inner layer that is positioned over the breasts of the wearer, and the other end of the first and second straps terminates in fabric that covers the back of said wearer;

wherein said outer layer is a solid piece of fabric that covers the breasts of the wearer, said outer layer being coupled to the fabric that covers the back of said wearer at each side of the wearer, and the detachable clasps connecting the outer layer to each of the first and second straps over each shoulder of the wearer and wherein the outer layer terminates in a seam to an abdominal portion of the tank, wherein the outer layer and the abdominal portion of the tank are connected to a back piece of fabric of the tank, the back piece of fabric being connected to the fabric that covers the back of said wearer;

a middle layer that is detachable by a clasp from the inner layer in two positions, each of the two positions being over each breast, the middle layer having one horizontal opening over each nipple of the wearer that is approximately one inch in length, said one opening being capable to receive a funnel portion of a breast pump and said one opening being able to support the funnel of the breast pump without assistance from the wearer when the middle layer is attached to the inner layer;

an inner layer having a two large openings through which each nipple and breast may be exposed when the middle layer and outer layer are detached at the detachable clasps of the outer layer and at one of the two positions of the middle layer such that the wearer may nurse an infant;

wherein the inner and middle layer terminate in an elastic band that extends around the wearer to support the breasts, and the middle layer is attached to the inner layer with a seam located in the middle of the chest of the wearer, the seam extending from the top of the inner layer to the elastic band.

18. The nursing garment of claim 17, wherein the detachable clasp comprises a male and female piece.

19. The nursing garment of claim 17, wherein the clasp at the at least two positions of the middle layer comprises a hook and eye closure.

* * * * *